United States Patent [19]

Hasson

[11] Patent Number: 5,658,272
[45] Date of Patent: *Aug. 19, 1997

[54] SURGICAL INSTRUMENT SUPPORT AND METHOD OF USING THE SAME

[76] Inventor: Harrith M. Hasson, 2043 N. Sedgwick, Chicago, Ill. 60614

[*] Notice: The term of this patent shall not extend beyond the expiration date of Pat. No. 5,201,742.

[21] Appl. No.: 392,272

[22] Filed: Feb. 21, 1995

Related U.S. Application Data

[63] Continuation of Ser. No. 130,582, Oct. 1, 1993, abandoned, which is a continuation-in-part of Ser. No. 945,237, Sep. 15, 1992, abandoned.

[51] Int. Cl.[6] ............................................. A61B 19/00
[52] U.S. Cl. ........................ 606/1; 606/108; 606/130; 606/192
[58] Field of Search ............................... 606/1, 108, 130, 606/185; 604/116, 164, 264; 128/749

[56] References Cited

U.S. PATENT DOCUMENTS

| | | | |
|---|---|---|---|
| 2,697,433 | 12/1954 | Zehnder | 606/130 |
| 3,017,887 | 1/1962 | Heyer | 606/130 |
| 3,021,842 | 2/1962 | Flood | 606/130 |
| 3,115,140 | 12/1963 | Volkman | 606/130 |
| 3,893,446 | 7/1975 | Miller . | |
| 4,493,707 | 1/1985 | Ishihara . | |
| 4,809,694 | 3/1989 | Ferrara | 606/130 |
| 5,002,557 | 3/1991 | Hasson . | |
| 5,030,223 | 7/1991 | Anderson et al. . | |
| 5,056,523 | 10/1991 | Hotchkiss, Jr. et al. . | |
| 5,100,411 | 3/1992 | Koutrouvelis . | |
| 5,147,316 | 9/1992 | Castillenti . | |
| 5,176,697 | 1/1993 | Hasson et al. . | |
| 5,201,742 | 4/1993 | Hasson . | |
| 5,263,956 | 11/1993 | Nobles | 606/1 |

FOREIGN PATENT DOCUMENTS

1680085A1  8/1986  U.S.S.R. .

*Primary Examiner*—Glenn Dawson
*Attorney, Agent, or Firm*—Wood, Phillips, VanSanten, Clark & Mortimer

[57] ABSTRACT

A support for a surgical instrument, having a base that defines a seat with a concave surface and a flat surface facing in a first direction for placement against tissue and a connector having a convex surface to abut to and move universally relative to the concave base surface. A sleeve with a passage through which a surgical instrument can be directed is attached to the connector such that the sleeve follows universal movement of the connector relative to the base. Cooperating structure on the connector and base maintains the connector and base in an operative position in which the convex surface on the connector resides adjacent to the plane of the flat base surface and does not project significantly in the first direction beyond the flat base surface.

18 Claims, 4 Drawing Sheets

SURGICAL INSTRUMENT SUPPORT AND METHOD OF USING THE SAME

CROSS-REFERENCE

This application is a continuation of application Ser. No. 08/130,582, filed Oct. 1, 1993, now abandoned which is a continuation-in-part of application Ser. No. 07/945,237, filed Sep. 15, 1992, entitled "Support for Surgical Instrument", now abandoned.

BACKGROUND OF THE INVENTION

1. Field of the Invention

This invention relates to surgical instruments and, more particularly, to a support for a laparoscopic surgical instrument to maintain a desired orientation of the instrument relative to a tissue through which the instrument extends.

2. Background Art

In performing laparoscopic surgery, an incision is made in a patient to admit a cannula which serves as a conduit for the introduction of selected surgical instruments into a body cavity. The body cavity in which the operation is performed is filled with a gas to distend the surrounding tissue to create a suitably sized operating space.

The inventor herein has designed structures to maintain the gas in the body cavity while allowing freedom of tilting movement for the surgical instrument. One such structure is shown in U.S. Pat. No. 5,002,557. This particular structure utilizes an elongate sleeve having an inflatable bladder at its distal end which is passed through the tissue into the body cavity. A collar with a conical sealing surface is slidable lengthwise of the sleeve. The distal end of the sleeve is passed through the tissue with the bladder deflated. Inflation of the bladder creates an annular shoulder which can be drawn up sealingly against the inside tissue surface. The collar is pressed into the tissue towards the bladder shoulder so that the bladder shoulder and collar captively embrace the tissue to thereby hold the sleeve in an operative position. The conical collar surface and bladder maintain a seal at the tissue incision even with the sleeve reoriented in use.

While the above structure affords a high integrity seal through a wide range of movement for the sleeve, it has one limitation. The basic instrument in U.S. Pat. No. 5,002,557 does not have any structure for maintaining a desired orientation of the sleeve. This feature is desirable to perform many conventional procedures. It is common to align the sleeve opening with a site at which more than one procedure is to be performed. The surgeon is usually required to remove and reinsert the same or different instruments. In the absence of some type of aligning structure for the sleeve, the surgeon is required to constantly manipulate the sleeve to access the same site. This is an inconvenience and time consuming. Further, certain procedures require the use of multiple instruments directed through separate incisions into a body cavity. The freely movable sleeves may reposition to cause interference between the various instruments therewithin. Furthermore, the conical structure limits the degree to which the sleeve can be tilted as the large end of the cone impinges on the opposing surface of the skin on the side to which the instrument is tilted.

The inventor herein has also developed certain guide structures in the form of adjustable jigs that can cooperate with an instrument. Exemplary structures are shown in my U.S. Pat. No. 5,201,742, entitled "Support Jig for a Surgical Instrument".

While the jig disclosed in U.S. Pat. No. 5,201,742 is was highly effective in terms of its versatility and stability, it has one drawback; that being that the tissue is required to flex significantly as the instrument is repositioned, due to the fact that the pivot point for the instrument is spaced a substantial distance away from the tissue.

SUMMARY OF THE INVENTION

The present invention is specifically directed to overcoming the above-enumerated problems in a novel and simple manner.

In one form of the invention, a support is provided for a surgical instrument, which support has: a base that defines a seat with a concave surface and has a flat surface facing in a first direction for placement against tissue: a connector having a convex surface to abut to and move universally relative to the concave base surface; a sleeve defining a passage through which a surgical instrument can be directed; structure for connecting the connector to the sleeve so that the sleeve follows universal movement of the connector relative to the base; and cooperating structure on the connector and base for maintaining the connector and base in an operative position in which the convex surface on the connector resides adjacent to the plane of the flat base surface and does not project significantly in the first direction beyond the flat base surface.

Because the convex surface is adjacent to the point of connection of the support to tissue, pivoting of an instrument on the support can occur with a relatively small incision without significantly stretching the tissue around the incision.

To facilitate connection between the connector and sleeve, a snap-fit arrangement can be provided.

The sleeve has an axial extent and an outer surface. Structure is provided on the sleeve that can be placed selectively in a) a first position to define an axially facing shoulder and b) a second position wherein it does not project significantly radially beyond the outer surface of the sleeve. The sleeve cooperates between at least one of the connector and base to selectively mount the sleeve and base in first and second different relative positions. In the first relative position, the shoulder is a first distance away from the flat base surface. In the second position, the shoulder is a second distance away from the flat base surface.

The shoulder can be defined by a bladder that is selectively inflatable and deflatable to be placed in its first and second positions.

With this arrangement, the surgical support can positively capture tissue to afford a stable support for an instrument.

The base establishes a significant contact area between the instrument support and tissue on which it is carried and thereby resists tipping of the support. The tissue engaging surface can be square, rectangular, round, or other suitable shape. Preferably, the effective diameter of the surface, which contacts the tissue, is between 4 and 9 cm, although other dimensions are contemplated.

The instrument support can be maintained in a number of different positions. The connector and sleeve can be selectively fixed as can the connector and base. This can be accomplish through a set screw, or other suitable structure.

In one form, the convex surface is part of a spherical outer surface on the connector and a line tangent to the spherical outer surface at a fight angle to the plane of the flat base surface intercepts the flat base surface. This arrangement affords a substantial contact area between the base and tissue.

In one form of the invention, the diameter of the spherical outer surface is at least two times the diameter of the sleeve.

In another form of the invention, a support is provided for a surgical instrument, which support has: a base with a substantially flat surface facing in a first direction for placement against tissue; a connector having a spherical outer surface and through bore; and cooperating structure on the base and connector for mounting the base and connector in an operative position in which the connector is universally movable relative to the base and the spherical outer surface of the connector resides adjacent to the plane of the flat base surface and does not project significantly in the first direction beyond the flat base surface.

The invention further contemplates a method of defining a passageway through a tissue to accommodate a surgical instrument, which method includes the steps of making an incision in the tissue, placing a base with an opening therethrough against the tissue so that the incision is exposed at the base opening, directing a sleeve through the base opening and tissue so that a portion of the sleeve is in a cavity bounded by the tissue, defining a first shoulder on the portion of the sleeve in the cavity, drawing the sleeve out of the incision to bear the shoulder on the sleeve portion against the tissue, providing a connector on the sleeve and sliding the connector along the sleeve to bear the connector against the base at a location adjacent to the tissue to thereby bring the first shoulder and base firmly against the tissue to captively hold the tissue; and fixing the connector relative to the sleeve.

The sleeve can be preassembled to the base so that the sleeve and base are movable as a unit as the sleeve is directed through the incision. Alternatively, the base, by itself, can be pre-applied on the tissue.

At least one of the connector and sleeve can be fixed as desired to the base.

The invention further contemplates a method, as described above, wherein the connector is slid along the sleeve to bear the connector against the tissue to thereby firmly hold the tissue between the connector and first shoulder. The connector can thus be used to perform a sealing function and at the same time guide movement of the sleeve associated therewith relative to the base.

DETAILED DESCRIPTION OF THE DRAWINGS

Figure 7:
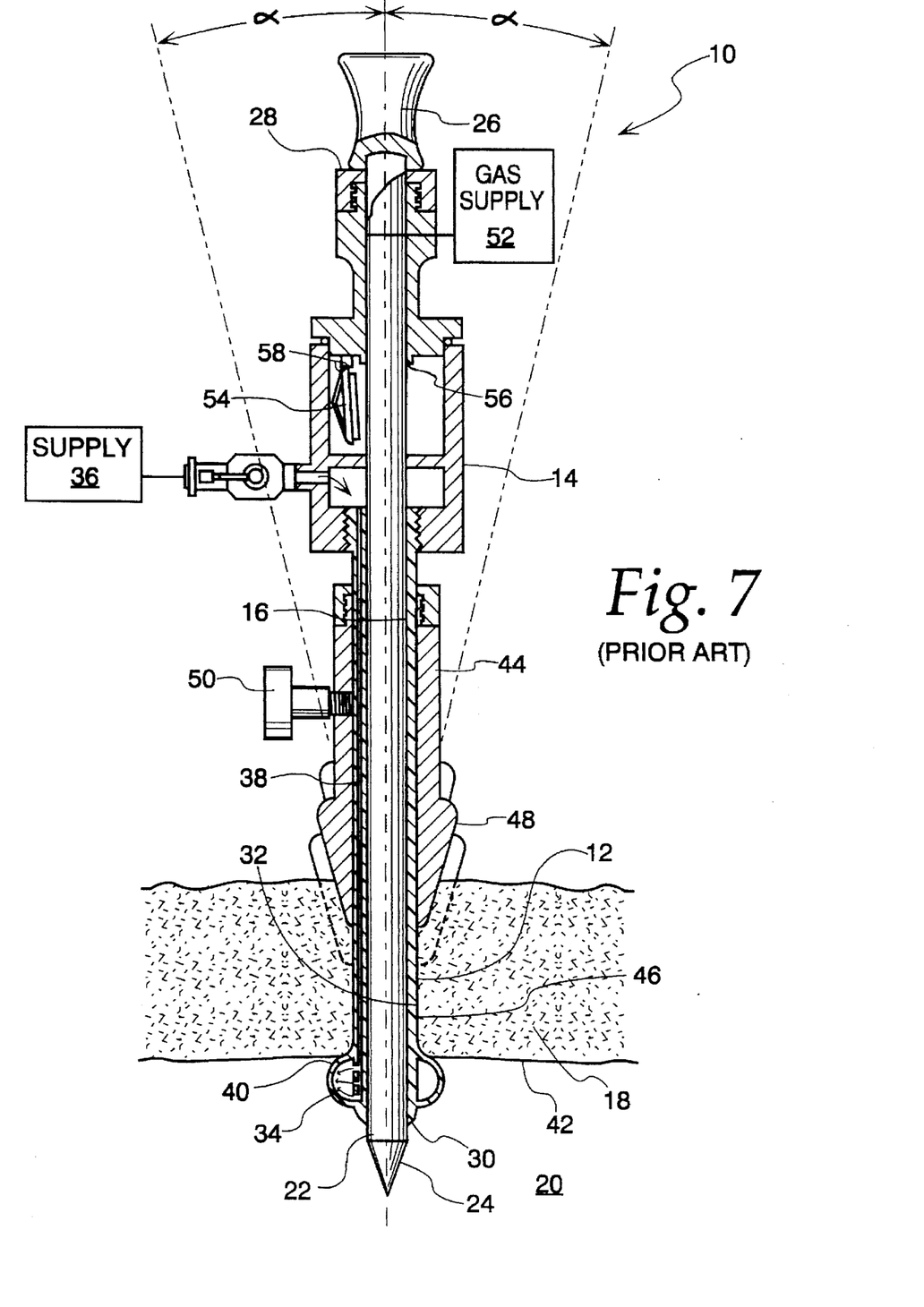
FIG. 7 is a sectional view of a prior art surgical instrument support in operative relationship to a tissue.

In FIG. 7, a prior art surgical instrument support is shown at 10. The support 10 has a sleeve 12 and housing 14 which cooperatively define a passageway 16 for a surgical instrument through a body tissue 18 into a cavity 20. A spike 22 with a sharpened distal end 24 is directed through the passageway 16 until an enlarged head 26 thereon abuts a shoulder 28 at the top of the housing 14. In this position, the sharpened distal end 24 protrudes from the free end 30 of the sleeve 12. The projecting, sharpened distal end 24 facilitates insertion of the instrument support 10 through a small incision 32 in the tissue 18.

The free end 30 of the sleeve 12 is advanced through the tissue 18 sufficiently that a bladder 34 thereon is fully exposed within the cavity 20. The bladder 34 is in a collapsed state as the sleeve 12 is directed through the tissue 18. Thereafter, the bladder 34 is inflated to the FIG. 7 configuration by fluid from a pressurized supply 36 which communicates through a passageway 38 integrally formed with the sleeve 12. The inflated bladder 34 defines an annular shoulder 40 which bears on the inside surface 42 of the tissue 18 to thereby prevent withdrawal of the sleeve 12 from the incision 32.

A collar 44 surrounds the sleeve 12 and is guided along the outer surface 46 thereof for movement lengthwise of the sleeve 12. The collar has a conical sealing surface 48 that can be pressed into the tissue 18. The surface 48 and surface 40 capture the tissue 18 and provide an effective seal around the incision 32. A set screw 50 can be tightened to lock the collar 44 to thereby maintain the instrument 10 in its operative position.

Once the collar 44 is locked, the spike 22 can be withdrawn. A gas, from a supply 52, can be introduced into the cavity 20 through the passageway 38 to distend the cavity 20 and define a suitable working area in the cavity 20. A hinged door 54 is abuttable to an annular shoulder 56 to seal the passageway 38. The door 54 is normally biased by a spring 58 into its sealing position. Entry of an instrument automatically pivots the door 54 into its open position shown in FIG. 7.

With the collar 44 locked in position, an effective seal is maintained by the sealing surface 48 and shoulder 40. This seal is maintained even as the sleeve 12 is tilted through a substantial angle, as indicated by the reference α. However, due to the resilience of the tissue 18, there is nothing to effectively stabilize the orientation of the support 10 in any one position. This problem is solved by the inventive instrument support shown at 60 in FIG. 1.

Figures 1, 2, 3, 4, 5, 6:
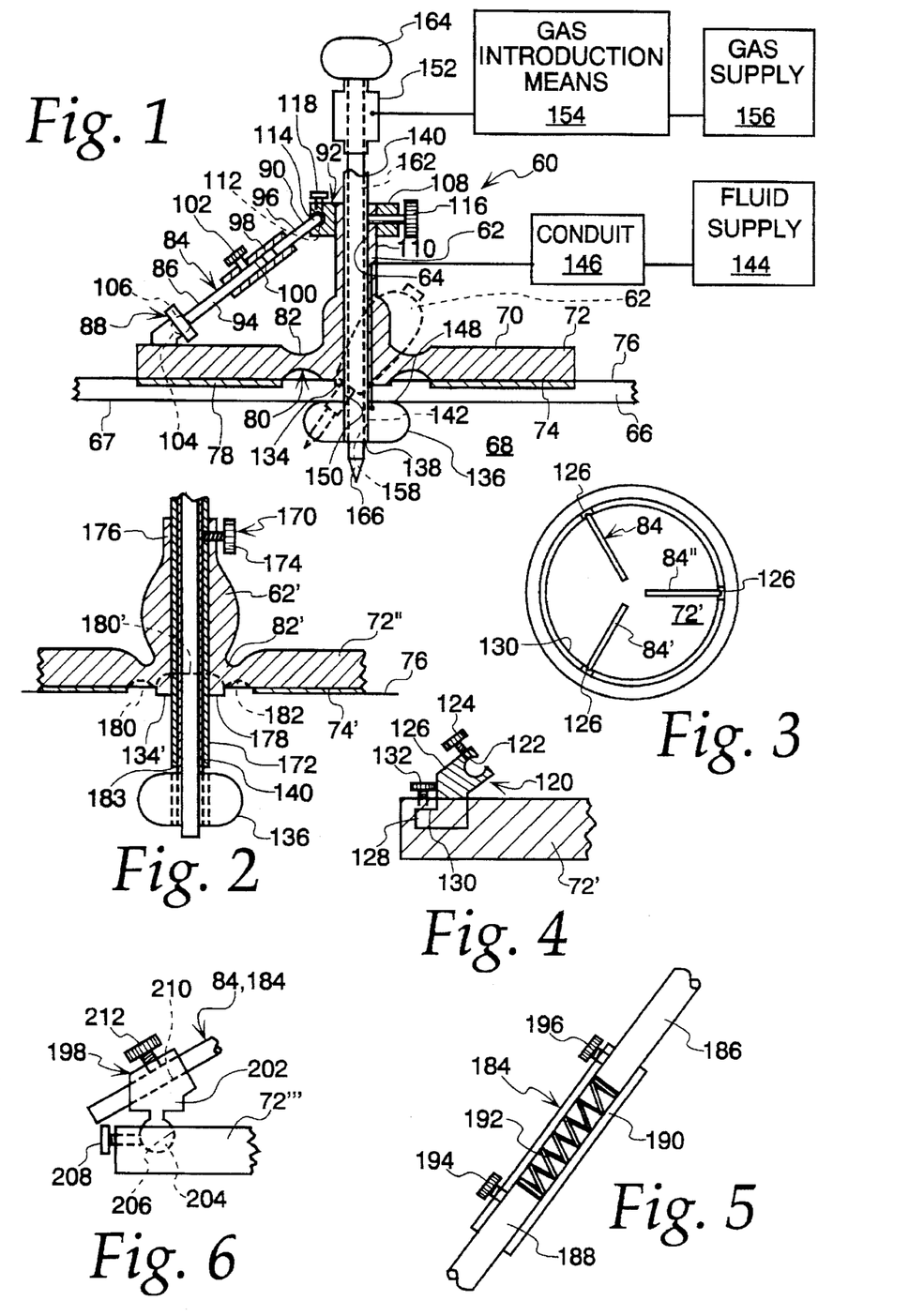
FIG. 1 is a sectional elevational view of a surgical instrument support according to the present invention in operative relationship to a tissue.
FIG. 2 is a view as in FIG. 1 and showing a modified form of surgical instrument support according to the present invention.
FIG. 3 is a schematic plan view of a surgical instrument support according to the present invention utilizing three extensible members for maintaining the orientation of a sleeve for an instrument on the support.
FIG. 4 is a fragmentary, partial cross-sectional view of a universal connection for an end of one of the extensible members.
FIG. 5 is a fragmentary, partial cross-sectional view of one form of extensible member that is normally biased to a predetermined length.
FIG. 6 is a fragmentary, perspective view of a modified form of universal connection for an end of one of the extensible members.

The instrument support 60 consists of a sleeve 62 having a through bore 64 defining a passageway for the introduction of an instrument from externally of a tissue 66 therethrough into a cavity 68. The sleeve 62 has an integrally formed means 70 for stabilizing the position of the sleeve 62 relative to the tissue 66. The means 70 is in the form of an annular plate 72 having an annular, flat surface 74 for facially engaging the tissue 66 with the support in an operative position. The surface 74 may be borne directly against a tissue surface 76 or, alternatively, an adhesive layer 78 can be interposed between the surface 74 and tissue 66 to releasably hold the plate 72 in a desired position relative to the tissue 66. The plate has a diameter that is preferably at least 1 inch and a thickness of at least ⅛ inch.

A means at 80 connects the plate 72 to the sleeve 62. The connecting means 80 is preferably integrally formed with the sleeve 62 and plate 72 from a rubber, or other deformable material. The connecting means 80 has a reduced thickness to produce a universal-type hinge 82 between the sleeve 62 and plate 72. This hinge 82 allows the This hinge 82 allows the sleeve 62 shown in phantom lines in FIG. 1.

The invention further contemplates a means at 84 for maintaining the sleeve 62 and plate 72 in a desired relationship. The maintaining means 84 is in the form of an elongate, extensible member/rod having a first end 86 connected to the plate 72 through a connecting means 88 and a second end 90 connected to the sleeve 62 through a connecting means 92.

The extensible rod 84 is defined by first and second cooperating parts 94, 96, respectively. A mounting sleeve 98 has a through bore 100 to accept both the first rod part 94 and second rod part 96. The second rod part 96 is suitably fixed to the mounting sleeve 98, as by welding. The other rod part 94 is freely slidable in and out of the through bore 100 so as to thereby vary the effective length of the extensible rod 84. A set screw 102 fixes the rod part 94 relative to the mounting sleeve 98 to maintain a desired effective length for the rod 84.

The connecting means 88 includes a socket 104 for reception of a ball 106 integrally formed at the end of the rod part 94. The rod end 86 is thus free to move universally relative to the plate 72.

The connecting means 92 includes a collar 108 which surrounds the outer surface 110 of the sleeve 62. The collar 108 has a socket 112 therein to receive a ball 114 on the rod end 90 to allow universal pivoting of the rod end 90 relative to the collar 108. The collar 108 is slidable axially relative to the sleeve 62 and can be fixed in a desired position by a set screw 116.

Once the plate 72 is abutted to the tissue 66, the sleeve 62 can be reoriented to align the passageway 64 defined thereby with a site at which a procedure is to be performed. This adjustment is permitted with the set screw 102 loosened. When the desired orientation of the sleeve 62 is arrived at, the set screw 102 is tightened to thereby fix the effective length of the mounting rod 84. For purposes of stability, at least two additional, similarly constructed mounting rods 84', 84" are provided as shown in FIG. 3. This arrangement produces a tripod support which adds significant stability to the sleeve 62.

To further stabilize the sleeve 62, a set screw 118 is provided to lock the ball 114 in the socket 112 to thereby prevent inadvertent movement of the rod end 90. The rod end 86 can be suitably fixed using a modified form of connecting means 120 as shown in FIG. 4. The connecting means 120 includes a socket 122 for reception of the ball 106 and a set screw 124 to lock the ball 106 in the socket 122. A similarly locking mechanism can be provided on one or both of the additional rods 84', 84".

Additional versatility is afforded by providing a movable base 126 as part of the connecting means 88, as shown in FIGS. 3 and 4. The base 126 has an L-shaped leg 128 which is received in a guide slot 130 in a plate 72'. The slot 130 extends circumferentially about the plate 72' to allow the relative circumferential position of the base 126 to be selected relative to the plate 72'. The set screw 132 associated with each base 126 allows the position of each base 126 relative to the plate 72' to be fixed. Similar legs 128 can be provided on the other rods 84', 84".

Another aspect of the invention is the provision of a sealing surface 134 formed integrally with the sleeve 62 to provide a seal at the tissue incision. The sealing surface 134, which may have a reduced diameter or be slightly tapered to penetrate the tissue 6, performs a function similar to the sealing surface 48 on the collar 44 on the prior art support 10 in FIG. 7.

To enhance the seal of the sealing surface 134, an inflatable bladder 136 is provided at the distal end 138 of a cylindrical guide sleeve/cannula 140 that can be made part of or fit within the sleeve 62. The bladder 136 is collapsible against the peripheral surface 142 of the cannula 140 and inflatable by a fluid from a supply 144 through an appropriate conduit 146. The inflatable bladder 136 defines an annular shoulder 148 which, in conjunction with the sealing surface 134, captively holds the tissue 66 and seals around an incision 150 through which the cannula 140 extends. The sleeve 62 can be maintained in a desired position relative to the cannula 140 by the set screw 116 or by a separate set screw which allows independent adjustment of the sleeve 62 and cannula 140 and collar 108 and sleeve 62.

The cannula 140 is associated with a housing 152 which has means 154 thereon to allow introduction of gas from a supply 156 to and through a passageway 158 defined by the cannula 140 into the cavity 68.

To attach the support 60 to the tissue 66, the bladder 136 is initially deflated and the set screws 102, 116; 118, 124 and 132 loosened. A spike 162 with an enlarged head 164 is extended through the cannula passageway 158 to expose a sharpened tip thereon at the distal end 138 of the cannula 140. The spike 162 and cannula 140 are then directed through the incision 150 until the bladder 136 is fully exposed in the cavity 68. Thereupon the bladder 136 is inflated to the configuration shown in FIG. 1. The cannula 140 is then pulled upwards until the inflated bladder 136 abuts the inside surface 67 of the tissue 66, anchoring the distal cannula end 138 inside the incision 150 and capturing the tissue 66 between the shoulder of the bladder 136 and the lower edge of the sealing surface 134 and lower surface 74 of the plate 72. The sleeve 62 is then slid down over the cannula 140 and squeezed against the tissue 66. The optional adhesive layer 78 firmly holds the plate 72 against the tissue 66. The orientation of the cannula 140 is then selected and maintained by tightening the several set screws 102, 116, 118, 124 and 132.

A modified form of support, according to the present invention, is shown at 170 in FIG. 2. The support 170 functions in the same manner as the support 60 and parts on the support 170 corresponding to those in the support 60 are similarly numbered in FIG. 2 including a "'" or a "''". In addition, a plastic or hard rubber sleeve 172 surrounds the cannula 140 and facilitates sliding movement of the sleeve 62' relative to the cannula 140. The plastic sleeve 172 is preferably adhered to one of the cannula 140 and sleeve 62'. The description below applies to the plastic sleeve 172 with the sleeve 172 adhered to the sleeve 62'. A set screw 174 extends through a reduced diameter portion 176 of the sleeve 62' and bears the plastic sleeve 172 frictionally against the cannula 140 to effect locking between the sleeve 62' and cannula 140.

The sleeve 62' is connected to a plate 72" through a hinge 82' as on the support 60. A projection 178 from the flat surface 74' of the plate 72" provides a reduced diameter sealing surface 134'. In this version, the projection 178 could be eliminated by extending the flat surface 74 in the same plane as shown by the dotted line 180 in FIG. 2 or the sleeve could be cut out as indicated by dotted lines 180'. In the former case, an annular undercut 182 in the surface 74' can be provided to facilitate the hinge action between the sleeve 62' and plate 72". The bladder 136 maintains the seal with the sleeve 62' with or without the projection 178.

The sleeve 172 also serves as an anchor to maintain the device within the incision. The sleeve 172 protrudes beyond the edge of the stabilizing plate 72" which impacts on the skin 76 by a fixed distance of about 6 min. By releasing the set screw 174 and sliding the sleeves 62', 172 downward until the surface 74' of the plate 72" abuts the skin surface 76, the leading edge of sleeve 172 will automatically project approximately 6–10 mm through the skin incision. The sleeve 172 is 1 mm in thickness, and thus the outside diameter of the sleeve 172 is approximately 2 mm greater than that of the cannula 140, allowing the sleeve 172 to wedge firmly into the skin to thereby act as an anchor and a seal. It should be noted that the leading edge 183 of the sleeve 172 extends generally only into the incision and does not reach the balloon.

The sleeve 172 alone can be relied upon to maintain the seal around the incision without either the bladder 136 or projection 178. The sleeve 172 extends lengthwise of the cannula sufficiently with the support 170 in its operative position to maximize the contact area between the tissue 66 surrounding the incision and the sleeve 172. Thus, the sleeve 172 serves a dual purpose.

A still further modification contemplated by the present invention is shown for the extensible rod 184, which can be used for one or all of the rods 84, 84', 84". The rod 184 has first and second relatively movable parts 186, 188 extendable within a sleeve 190. A coil spring 192 within the sleeve 190 biases the rod parts 186, 188 away from each other to place the rod 184 in an extended state. With three sets of reds 184 mounted as in FIG. 3, the spring action 192 normally urges the sleeve 62, 62' into an upright state i.e. with the axis thereof at right angles to the plane of the surface 74, 74'. This obviates the user's having to manually maintain the sleeve 62, 62' upright as the cannula position is set. Set screws 194, 196 are provided to releasably fix the position of the rod parts 186, 188 relative to the sleeve 190.

FIG. 6 shows a modified form of universal connection at 198 between an end of one of the rods 84, 184 and a modified form of plate 72'". The connection 198 includes a fitting 202 with an integral ball 204 that fits within a correspondingly configured recess 206 in the plate 72'" to allow guided universal movement between the fitting 202 and plate 72'". The fitting 202 can be locked by a set screw 208. The fitting 202 has a through bore 210 to allow the rod parts 94, 188 to be guided fully therethrough to extend the range of adjustment for the sleeve 62, 62'. A locking screw 212 allows the rod parts 94, 188 to be fixed to the fitting 202.

DESCRIPTION OF THE PREFERRED EMBODIMENT

Figure 8:
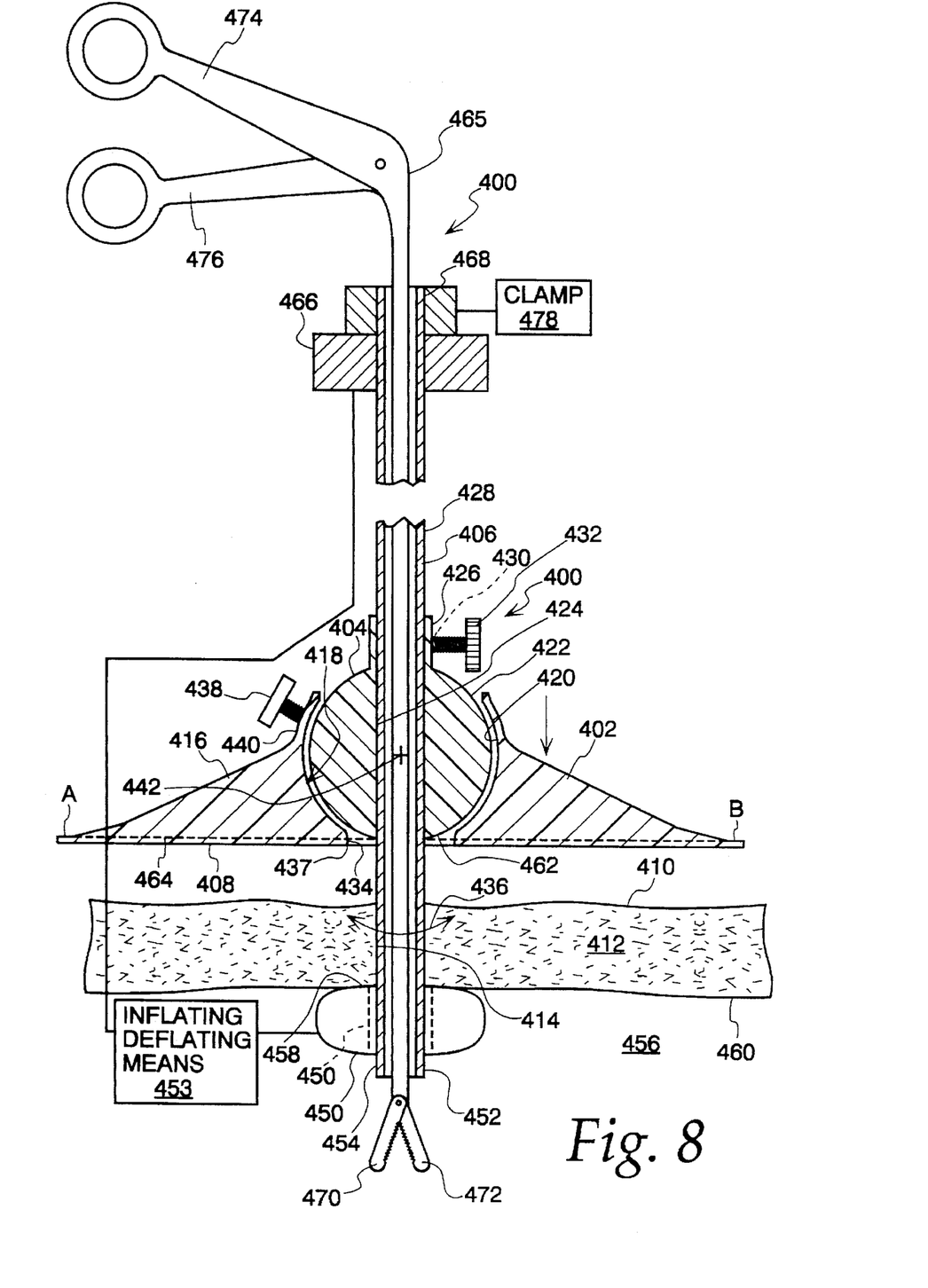
FIG. 8 is a cross-sectional view of a modified form of surgical instrument support, according to the present invention, being attached to a tissue, with a surgical instrument directed therethrough.
Figure 9:
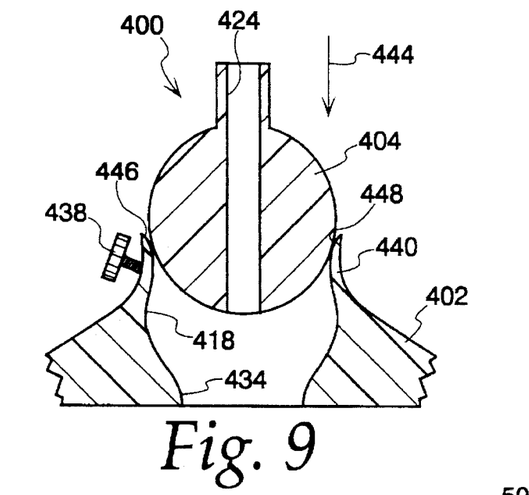
FIG. 9 is a cross-sectional view of a connector on the instrument support being snap-fit into its operative position with respect to a base.

A modified form of instrument support structure, according to the present invention, is shown at 400 in FIGS. 8 and 9. The instrument support structure 400 consists of a base 402, a connector 404 and a sleeve 406 shown in an operative position for the instrument support structure in FIG. 8.

The base 402 has a flat surface 408 to facially engage a surface 410 on a tissue 412 through which an incision 414 has been made. The base has a body 416 defining a receptacle 418 for the connector 404. The receptacle 418 is bounded by a concave surface 420 that is slightly larger than, but matched in shape to, the spherical outer surface 422 of the connector 404. With the connector 404 operatively positioned within the receptacle 418, the connector 404 pivots universally against and relative to the base 402.

The connector 404 has a through bore 424 which accepts the sleeve 406, which is preferably cylindrical, and slidable lengthwise within the through bore 424. The connector 404 has a cylindrical neck 426 which closely surrounds the sleeve outer surface 428. The neck 426 has a bore 430 therein to accept a set screw 432, which can be tightened to fix the relative positions of the connector 404 and sleeve 406.

The sleeve 406 thus follows the universal movement of the connector 404 relative to the base 402. This movement is accommodated by providing an enlarged bore 434 communicating from the receptacle 418 through the base 402, whereby the subassembly consisting of the connector 404 and sleeve 406 can pivot, as in the direction of double-headed arrow 436, within a range limited by an annular shoulder 436 surrounding the bore 434.

The relative positions of the base 402 and connector 404 can be fixed by a set screw 438 which is directed through an upper portion 440 of the base 402 and against the outer surface 422 of the connector 404 above the center point 442 so that the advancing set screw 438 cams the connector 404 progressively into the receptacle 418.

The upper portion 440 of the base 402 is made relatively thin, as from plastic, to be deformable sufficiently to allow the connector 404 to be snap-fit to the base 402. As the connector 404 is driven in the direction of the arrow 444 in FIG. 9, the restricted entryway 446 to the receptacle 418 is progressively enlarged by the connector outer surface 422 until the connector 404 fully seats in the receptacle, whereupon the base potion 440 springs back to its undeformed state, shown in FIG. 8. Camming open of the entryway 446 is facilitated by having an annular, tapered edge 448 at the entryway 446 to the receptacle 418. With this structure, the base 402 and connector 404 can be conveniently assembled on site by the surgeon.

The invention contemplates several different ways of setting up the instrument support structure 400. In one such method, the connector 404 is preassembled to the base 402, as shown in FIG. 9. The subassembly consisting of the base 402 and connector 404 is then placed against the tissue 412 so that the incision 414 coincides with the opening defined by the base bore 434.

The sleeve 406 can then be directed through the assembled base 402 and connector 404. The sleeve 406 has an inflatable bladder/membrane 450 at the distal end 452 thereof. The bladder/membrane 450 is selectively placed in an inflated state, as shown in solid lines in FIG. 8, and a collapsed state, as shown in phantom lines in FIG. 8. In this latter state, the bladder/membrane 450 does not project significantly outwardly from the peripheral sleeve surface 428.

The bladder/membrane 450 is placed selectively in its expanded and collapsed state by an inflating/deflating means, shown schematically at 453 in FIG. 8. The bladder/membrane 450 is initially deflated to allow the sleeve 406 to be directed through the connector 404 without interference between the bladder/membrane and the sleeve 406. The sleeve 406 is extended sufficiently through the connector 404 that a distal portion 454 thereon is fully exposed within a cavity 456 surrounded by the tissue 412. By then inflating the bladder/membrane 450 through the means 453, an annular shoulder 458 is defined by the bladder/membrane 450. The sleeve 406 can then be dram upwardly to bear the shoulder 458 against the inside surface 460 of the tissue 412. The subassembly, consisting of the base 402 and connector 404, is then slid downwardly towards the distal sleeve end 452 until the tissue 412 is firmly captured between the flat base surface 408 and the shoulder 458 on the bladder/membrane 450. By then tightening the set screw 432, the tissue 412 will remain positively captive between the base 402 and membrane/bladder 450.

According to the invention, it is preferred that the bottom edge 462 of the connector 404 be adjacent to the flat base surface 408 with the base 402 and connector 404 in operative relationship. The bottom edge 462 can be slightly above the surface 408, slightly therebelow, or flush therewith. If the base 402 were shortened in a vertical direction, as indicated by the phantom lines 464, the connector 404 would project slightly below the base surface 408 and would thus be urged directly against the tissue 412 as the support structure 400 is assembled to the tissue 412. This enhances both the stability of the support structure 400 and the integrity of the seal around the incision 414.

With the tissue 412 captive between the base 402 and bladder/membrane 450, the sleeve 406 can be tilted about its length by pivoting the connector 404 pivotably against the base surface 420. Once a desired relative position between the connector 404 and base 402 is established, the set screw 438 can be tightened.

With the support structure assembled, an instrument 465 can be directed through a seal 466, at the proximal end 468 of the sleeve 406, and the sleeve 406 to thereby enter the cavity 456. The sealing structure 466 could take any form known to those skilled in the art.

Similarly, the instrument 465 can take any of a number of different forms. As shown in the drawings, the instrument 465 is a forceps having jaws 470, 472 which are movable selectively towards and away from each other through the operation of separate control handles 474, 476, which remain at all times exposed at the proximal end 468 of the sleeve 406.

A clamp 478, of known construction can be used to fix the position of the instrument 465 relative to the sleeve 406.

When it is desired to change the orientation or the extension of the sleeve 406 within the cavity 456, the clamp 478, and set screws 432, 438 can be selectively released and reset after a desired new position is selected.

The invention contemplates other methods of setting up the instrument support structure 400. For example, the base 402 can be initially placed against a tissue 412, after which the connector 404 with the sleeve 406 already therein, can be snapped into the base 402 as the sleeve 406 is advanced through the tissue 412.

Still further, the base 402, connector 404 and sleeve 406 can all be preassembled before the sleeve 406 is directed through the tissue 4 12.

Figure 14:
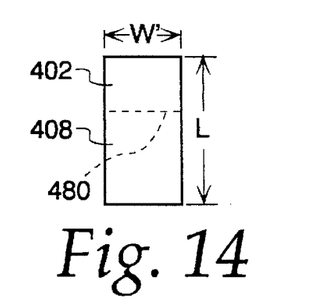
FIG. 14 is a schematic representation of the bottom cross-section of a tissue-engaging surface on a base on the support.

Regardless of the manner of assembly, the connector 404 firmly holds the connector 402 against the tissue 412 at a point adjacent thereto for maximum stability. The stability of the support structure 400 is further enhanced by configuring the base 402 so that the flat surface 408 thereon makes contact with the tissue 412 over a substantial area. In one form, the flat base surface 408 has a rectangular shape. It of course could be square, as indicated with dotted lines 480. A suitable dimension for the rectangular surface 408 in FIG. 14 has a width (W) of 6 cm and a length (L) of 9 cm. The length L for the plate 408 is preferably aligned to be parallel with the primary path of pivoting for the sleeve 406. This gives maximum stability to the base 402. As can be seen, with the rectangular base in place and the length of the base 402 aligned between the ends A and B in FIG. 8, any tendency to lift the end A is resisted by the end B digging into the tissue 412. Similarly, any tendency to lift end B is resisted by end A which digs into the tissue 412. Consequently, a substantial potion of the surface 408 remains in contact with the tissue 412, even as the sleeve 406 is moved and the base 402 tips in use.

Figure 15:
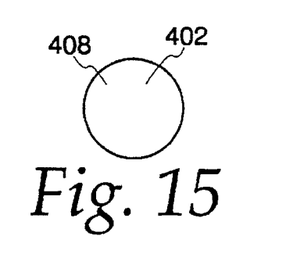
FIG. 15 is a view as in FIG. 14 showing a modified form of base.

FIG. 15 shows an alternative, circular shape for the base surface 408.

Regardless of the shape of the base 402, it is desired that the effective diameter (i.e. the distance from the center to the closest edge thereof) be on the order of 2–9 cm.

Figure 10:
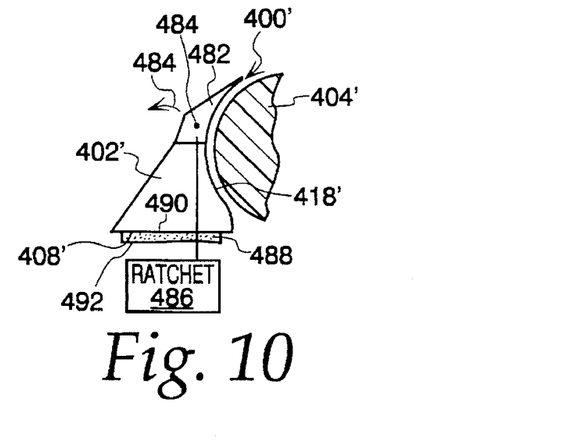
FIG. 10 is a fragmentary, partial cross-section view of a modified form of connection between a base and connector, according to the present invention.

The invention further contemplates various different structures to join a connector and base. In FIG. 10 a support structure 400' is shown including a connector 404' and a base 402'. The base 402' has one, and preferably a plurality, of tabs 482 which are each pivotable about a pin 484 between a holding position, shown in solid lines in FIG. 10, and a release position, wherein the tab 482 is pivoted in the direction of arrow 484 away from the connector 404 to allow the connector 404 to be separated from the base receptacle 418'. A ratchet mechanism 486 can be provided to releasably maintain the tabs 482 in their holding position.

The tabs 482 can be pivoted to a release position to allow introduction of the connector 404', after which the tabs 482 can be ratcheted into their holding position by a simple pressing step.

The support structure 400' also shows a layer 488, which has an adhesive on both sides 490, 492, to bond to the base surface 408' and the tissue 412. This gives even greater stability to the support structure 400' on the tissue 412.

Figure 12:
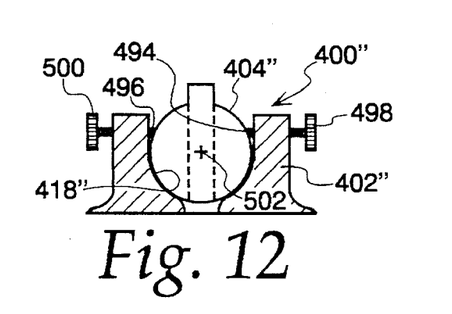
FIG. 12 is a cross-sectional view of a further modified form of connection between a base and connector.

FIG. 12 shows a modified form of support structure 400", wherein the base 402" defines a U-shaped receptacle 418", through which a connector 404" can pass, without interference, into the operative position shown in FIG. 12. Diametrically opposite tabs 494, 496 can be advanced by set screws 498, 500 at a location above the center 502 of the connector 404" to releasably maintain the connector 404" firmly in the receptacle 418".

Figure 11:
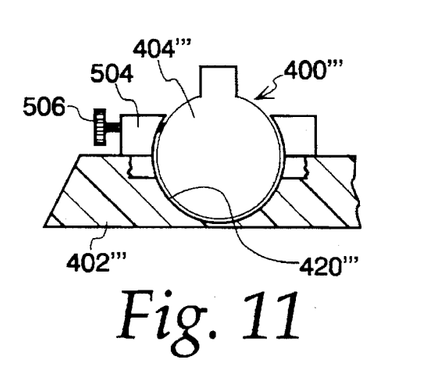
FIG. 11 is a view as in FIG. 10 of a further modified form of connection between a base and connector.

In FIG. 11, a modified form of support structure is shown at 400'", to include a base 402'" and a connector 404'". A cap 504 is threaded into the base 402'" to captively hold the connector 404'" in its operative position on the base 402'". By threading the cap 504 downwardly, the connector 404'" is pressed positively against the receptacle surface 420'" so that it is thereby fixed. An optional set screw 506 can be provided to more positively fix the relative positions of the connector 404'" on the base 402'".

Figure 13:
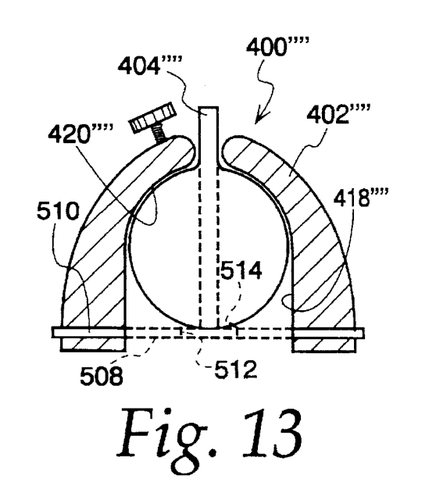
FIG. 13 is a cross-sectional view of a still further modified form of connection between a base and connector.

A further modified form of support structure is shown in FIG. 13 at 400"". A base 402"" has a downwardly opening, U-shaped receptacle 418"" which allows the connector 404"" to be directed upwardly into its operative position against a surface 420"" defined by the base 402"". Once the connector 404"" is seated in its operative position, a retaining plate 508 can be slid radially through a slot 510 in the base 402"". The plate 508 has a through opening 512 to accommodate an instrument extending through the connector 404"". The through opening 512 is bounded by an edge 514 which vertically supports the connector 404"" and guides the same as it pivots, in conjunction with the base surface 420"".

It is preferred that the diameter of the connectors 404, 404', 404", 404'", and 404"" be at least two times the diameter of the sleeve 406.

The foregoing disclosure of specific embodiments is intended to be illustrative of the broad concepts comprehended by the invention.

I claim:

1. A surgical instrument support comprising:

a base having a flat surface facing in a first direction for placement against a tissue, said base defining a seat with a concave surface, there being one piece defining at least a portion of each of the flat and concave base surfaces;

connector having a convex surface to abut to and move universally relative to the concave base surface;

sleeve defining a passage through which a surgical instrument can be directed;

means for connecting the connector to the sleeve so that the sleeve follows universal movement of the connector relative to the base; and first means cooperating between the connector and base for maintaining the connector and base in an operative position in which the convex surface on the connector resides adjacent to a plane within which the flat base surface resides and does not project significantly in the first direction beyond the flat base surface, said flat base surface defining the furthestmost extension of the support in the first direction, whereby the flat base surface can be pressed sealingly against a tissue through which an incision is to be made to allow a surgical instrument to be directed through the sleeve passage into an incision around which the flat base surface seals, wherein the first cooperating means comprises means for snap fitting the connector and sleeve into the operative position.

2. A surgical instrument support comprising:

a base having a flat surface facing in a first direction for placement against a tissue, said base defining a seat with a concave surface, there being one piece defining at least a portion of each of the flat and concave base surfaces;

a connector having a convex surface to abut to and move universally relative to the concave base surface;

a sleeve defining a passage through which a surgical instrument can be directed;

means for connecting the connector to the sleeve so that the sleeve follows universal movement of the connector relative to the base; and first means cooperating between the connector and base for maintaining the connector and base in an operative position in which the convex surface on the connector resides adjacent to a plane within which the flat base surface resides and does not project significantly in the first direction beyond the flat base surface, said flat base surface defining the furthestmost extension of the support in the first direction, whereby the flat base surface can be pressed sealingly against a tissue through which an incision is to be made to allow a surgical instrument to be directed through the sleeve passage into an incision around which the flat base surface seals, wherein the sleeve has an axial extent and an outer surface, there being second means on the sleeve selectively positionable between a) a first position wherein the second means defines an axially facing shoulder that projects radially beyond the outer surface of the sleeve and b) a second position wherein the second means does not project significantly radially beyond the outer surface of the sleeve, and third means cooperating between the sleeve and at least one of the connector and base for selectively mounting the sleeve and base in first and second different relative positions, with the shoulder of the second means being spaced axially from the flat base surface a first distance with the base and sleeve in said first relative position and the connector and sleeve in an operative relationship and the second means being spaced axially from the flat base surface a second distance with the base and sleeve in said second relative position and the connector and sleeve in an operative relationship.

3. The surgical instrument support according to claim 2 wherein the third means includes fourth means for releasably fixing the relative position of the connector and sleeve and fifth means for releasably fixing the relative positions of the connector and base.

4. The surgical instrument support according to claim 3 wherein at least one of the fourth and fifth means comprises a set screw that is extendable in a line transversely to a line perpendicular to the plane of the flat base surface.

5. The surgical instrument support according to claim 2 wherein the second means comprises a bladder that is selectively inflatable and deflatable to be placed in its first and second positions, respectively.

6. A surgical instrument support comprising:

base having a flat surface facing in a first direction for placement against a tissue, said base defining a seat with a concave surface, there being one piece defining at least a portion of each of the flat and concave base surfaces;

a connector having a convex surface to abut to and move universally relative to the concave base surface;

a sleeve defining a passage through which a surgical instrument can be directed;

means for connecting the connector to the sleeve so that the sleeve follows universal movement of the connector relative to the base; and first means cooperating between the connector and base for maintaining the connector and base in an operative position in which the convex surface on the connector resides adjacent to a plane within which the flat base surface resides and does not project significantly in the first direction beyond the flat base surface, said flat base surface defining the furthestmost extension of the support in the first direction, whereby the flat base surface can be pressed sealingly against a tissue through which an incision is to be made to allow a surgical instrument to be directed through the sleeve passage into an incision around which the flat base surface seals, wherein said convex surface is part of a spherical outer surface on the connector and a line tangent to said spherical outer surface at a right angle to the plane within which the flat base surface resides intercepts the flat base surface wherein each of the connector and flat base surface has a diameter and the diameter of the flat base surface is at least two times the diameter of the connector.

7. A support for a surgical instrument, said support comprising:

a base having a substantially flat surface facing in a first direction for placement against a tissue;

a connector having a spherical outer surface and a through bore; and first means cooperating between the base and connector for snap fitting the base and connector together in an operative position in which the connector is universally movable relative to the base and the spherical outer surface of the connector resides adjacent to a plane within which the flat base surface resides and does not project significantly in the first direction beyond the flat base surface.

8. A support for a surgical instrument, said support comprising:

a base having a substantially flat surface facing in a first direction for placement against a tissue;

a connector having a spherical outer surface and a through bore;

first means cooperating between the base and connector for snap fitting the base and connector together in an operative position in which the connector is universally movable relative to the base and the spherical outer surface of the connector resides adjacent to the plane of the flat base surface and does not project significantly in the first direction beyond the flat base surface; and second means cooperating between the base and connector for fixing the base and connector selectively in a plurality of different positions.

9. The surgical instrument support according to claim 8 wherein the second means comprises a set screw.

10. A support for a surgical instrument, said support comprising:

a base having a substantially flat surface facing in a first direction for placement against a tissue;

a connector having a spherical outer surface and a through bore;

first means cooperating between the base and connector for snap fitting the base and connector together in an operative position in which the connector is universally movable relative to the base and the spherical outer surface of the connector resides adjacent to a plane within which the flat base surface resides and does not project significantly in the first direction beyond the flat base surface; and second means mounted to at least one of the base and connector for defining a first shoulder facing the flat base surface to captively hold a tissue between the first shoulder and the flat base surface.

11. The surgical instrument support according to claim 10 wherein the second means comprises a sleeve with a flexible bladder thereon that defines said first shoulder.

12. A support for a surgical instrument, said support comprising:

a base having a substantially flat surface fitting in a first direction for placement against a tissue;

a connector having a spherical outer surface and a through bore:

first means cooperating between the base and connector for snap fitting the base and connector together in an operative position in which the connector is universally movable relative to the base and the spherical outer surface of the connector resides adjacent to a plane within which the flat base surface resides and does not project significantly in the first direction beyond the flat base surface, wherein the flat base surface has one of a square and rectangular shape as viewed at a right angle to the plane of the flat base surface.

13. A method of defining a passageway through a tissue to accommodate a surgical instrument, said method comprising the steps of:

making an incision in the tissue;

placing a base with an opening therethrough against the tissue so that the incision is exposed at the base opening;

directing a sleeve through the base opening and tissue so that a portion of the sleeve is in a cavity bounded by the tissue;

defining a first shoulder on the portion of the sleeve in the cavity;

drawing the sleeve out of the incision to bear the shoulder on the sleeve portion against the tissue;

providing a connector on the sleeve and sliding the connector along the sleeve to bear the connector against the base at a location adjacent to the tissue and thereby bring the first shoulder and base firmly against the tissue to captively hold the tissue; and fixing the connector relative to the sleeve.

14. The method of defining a passageway through a tissue according to claim 13 including the step of fixing at least one of the connector and sleeve to the base.

15. A method of defining a passageway through a tissue to accommodate a surgical instrument, said method comprising the steps of:

making an incision in the tissue;

placing a base with an opening therethrough against the tissue so that the incision is exposed at the base opening;

directing a sleeve through the base opening and tissue so that a portion of the sleeve is in a cavity bounded by the tissue;

defining a first shoulder on the portion of the sleeve in the cavity;

drawing the sleeve out of the incision to bear the first shoulder on the sleeve portion against the tissue;

providing a connector on the sleeve and sliding the connector along the sleeve to bear the connector against the tissue to thereby firmly hold the tissue between the connector and first shoulder; and guiding pivoting movement of the connector on the base.

16. The method of defining a passageway through a tissue according to claim 15 including the step of fixing the connector, sleeve, and base, each relative to the other.

17. A support for a surgical instrument, said support comprising:

a base having a flat surface facing in a first direction for placement against a tissue, said base defining a seat with a concave surface;

a connector having a convex surface to abut to and move universally relative to the concave base surface;

a sleeve defining a passage through which a surgical instrument can be directed;

means for connecting the connector to the sleeve so that the sleeve follows universal movement of the connector relative to the base; and first means cooperating between the connector and base for maintaining the connector and base in an operative position in which the convex surface on the connector resides adjacent to a plane within which the flat base surface resides and does not project significantly in the first direction beyond the flat base surface, said first cooperating means comprising means for snap fitting the connector and sleeve into the operative position.

18. A support for a surgical instrument, said support comprising:

a base having a flat surface facing in a first direction for placement against a tissue, said base defining a seat with a concave surface; a connector having a convex surface to abut to and move universally relative to the concave base surface;

a sleeve defining a passage through which a surgical instrument can be directed;

means for connecting the connector to the sleeve so that the sleeve follows universal movement of the connector relative to the base; and first means cooperating between the connector and base for releasably fixedly maintaining the connector and base in an operative position in which the convex surface on the connector resides adjacent to a plane within which the flat base surface resides and does not project significantly in the first direction beyond the flat base surface, said first cooperating means comprising means for snap fitting the connector and sleeve into the operative position.

* * * * *